(12) United States Patent
Ramella-Roman et al.

(10) Patent No.: US 11,170,199 B1
(45) Date of Patent: Nov. 9, 2021

(54) SYSTEMS AND METHODS FOR VISUALIZING ELASTIN AND COLLAGEN IN TISSUE

(71) Applicants: Jessica Claudia Ramella-Roman, Miami, FL (US); Camilo Roa, Miami, FL (US); Vinh Du Le, Miami, FL (US); Ilyas Saytashev, Miami, FL (US)

(72) Inventors: Jessica Claudia Ramella-Roman, Miami, FL (US); Camilo Roa, Miami, FL (US); Vinh Du Le, Miami, FL (US); Ilyas Saytashev, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/342,054

(22) Filed: Jun. 8, 2021

(51) Int. Cl.
*G06K 9/00* (2006.01)
*G16H 30/40* (2018.01)
*G06N 3/08* (2006.01)

(52) U.S. Cl.
CPC ....... *G06K 9/0014* (2013.01); *G06K 9/00147* (2013.01); *G06N 3/08* (2013.01); *G16H 30/40* (2018.01)

(58) Field of Classification Search
CPC .. G06K 9/0014; G06K 9/00147; G16H 30/40; G06N 3/08
See application file for complete search history.

(56) References Cited

U.S. PATENT DOCUMENTS

| 2011/0184260 A1* | 7/2011 | Robinson | G01J 3/02 600/316 |
| 2015/0080744 A1 | 3/2015 | Li et al. | |

OTHER PUBLICATIONS

Keikhosravi et al., "Non-disruptive collagen characterization in clinical histopathology using cross-modality image synthesis", Commun Biol 3, 414 (2020), pp. 1-12 (Year: 2020).*
Wood et al., "Polarized light propagation in multiply scattering media exhibiting both linear birefringence and optical activity: Monte Carlo model and experimental methodology," Journal of Biomedical Optics, Jan./Feb. 2007, pp. 014029-1-014029-10, vol. 12, No. 1.
Ghassemi et al., "A new approach for optical assessment of directional anisotropy in turbid media," Journal of Biophotonics, Jan. 20, 2015, pp. 1-9.
Ghassemi et al., "Out-of-plane stokes imaging polarimeter for early skin cancer diagnosis," Journal of Biomedical Optics, Jul. 2012, pp. 076014-1-076014-9, vol. 17, No. 7.

(Continued)

*Primary Examiner* — Nay A Maung
*Assistant Examiner* — Jose M Torres
(74) *Attorney, Agent, or Firm* — Saliwanchik, Lloyd & Eisenschenk

(57) ABSTRACT

Systems and methods for visualizing, and/or determining the amount of, collagen and elastin in tissue are provided. Training data can be generated using Mueller matrix polarimetry microscopy data, combined with second harmonic generation (SHG) and/or two photon excitation fluorescence (TPEF) microscopy data as ground truth. The SHG and/or TPEF data can be used to train a neural network for feature extraction, and classification can be performed. The components and decompositions of the Mueller matrix data can be arranged as individual channels of information, forming one voxel per sample.

20 Claims, 10 Drawing Sheets

(56) References Cited

OTHER PUBLICATIONS

Ramella-Roman et al., "Design, testing, and clinical studies of a handheld polarized light camera," Journal of Biomedical Optics, Nov./Dec. 2004, pp. 1305-1310, vol. 9, No. 6.

Ghassemi et al., "A polarized multispectral imaging system for quantitative assessment of hypertrophic scars," Biomedical Optics Express, Oct. 1, 2014, pp. 3337-3354, vol. 5, No. 10.

Drezek et al., "Understanding the contributions of NADH and collagen to cervical tissue fluorescence spectra: modeling, measurements, and implications," Journal of Biomedical Optics, Oct. 2001, pp. 385-396, vol. 6, No. 4.

Gan et al., "Analyzing three-dimensional ultrastructure of human cervical tissue using optical coherence tomography," Biomedical Optics Express, Apr. 1, 2015, pp. 1090-1108, vol. 6, No. 4.

Foxman et al., "Use of the fetal fibronectin test in decisions to admit to hospital for preterm labor," Clinical Chemistry, Feb. 2004, pp. 663-665, vol. 50, No. 3.

Myers et al., "The mechanical role of the cervix in pregnancy," Journal of Biomechanics, Jun. 25, 2015, pp. 1-29, vol. 48, No. 9, Author Manuscript.

Iams et al., "Care for women with prior preterm birth," American Journal of Obstetrics and Gynecology, Aug. 2010, pp. 1-21, vol. 203, No. 2, Author Manuscript.

Bishop, "Pelvic scoring for elective induction," Obstetrics and Gynecology, Aug. 1964, pp. 266-268, vol. 24, No. 2.

Vink et al., "Cervical etiology of spontaneous preterm birth," Seminars in Fetal and Neonatal Medicine, Apr. 2016, pp. 1-17, vol. 21, No. 2, Author Manuscript.

Stoff et al., Cervical Collagen Imaging for Determinign Preterm Labor Risks Using a Colposcope with Full Mueller Matrix Capability, Proc. SPIE 9689, Photonic Therapeutics and Diagnostics XII, 968947, Mar. 8, 2016, 6 pages.

Goldenberg et al., "Epidemiology and causes of preterm birth," Lancet, Jan. 5, 2008, pp. 75-84, vol. 371.

Esplin, "Preterm birth: a review of genetic factors and future directions for genetic study," Obstetrical and Gynecological Survey, Dec. 2006, pp. 800-806, vol. 61, No. 12.

Hamilton et al., "Births: preliminary data for 2015," National Vital Statistics Reports, Jun. 2, 2016, pp. 1-15, vol. 65, No. 3.

Bloomfield, "How is maternal nutrition related to preterm birth," Annual Review of Nutrition, May 2011, pp. 235-261, vol. 31.

Word et al., "Dynamics of cervical remodeling during pregnancy and parturition: mechanisms and current concepts," Seminars in Reproductive Medicine, Jan. 2007, pp. 69-79, vol. 25, No. 1.

Reiter et al., "Digital examination and transvaginal scan—competing or complementary for predicting preterm birth," Acta Obstetricia et Gynecologica Scandinavica, Apr. 2012, pp. 428-438, vol. 91.

Daskalakis et al., "Fetal fibronectin as a predictor of preterm birth," Journal of Obstetrics and Gynaecology, Jul. 2000, pp. 347-353, vol. 20, No. 4.

Albers, "Monitoring the fetus in labor: evidence to support the methods," Journal of Midwifery and Women's Health, Nov./Dec. 2001, pp. 366-373, vol. 46, No. 6.

Thacker et al., "Continuous electronic heart rate monitoring for fetal assessment during labor," The Cochrane Database of Systematic Reviews, Apr. 2001, pp. 1-6, No. 2.

Kleissl et al., "Collagen changes in the human uterine cervix at parturition," American Journal of Obstetrics and Gynecology, Apr. 1, 1978, pp. 748-753, vol. 130, No. 7.

Granstrom et al., "Changes in the connective tissue of corpus and cervix uteri during ripening and labour in term pregnancy," British Journal of Obstetrics and Gynaecology, Oct. 1989, pp. 1198-1202, vol. 96.

Anastasiadou et al., "Polarimetric imaging for the diagnosis of cervical cancer," Physica Status Solidi (C), Mar. 2008, pp. 1423-1426, vol. 5, No. 5.

Dillet et al., "Size determination by use of two-dimensional mueller matrices backscattered by optically thick random media," Applied Optics, Jul. 2006, pp. 4669-4678, vol. 45, No. 19.

Lu et al., "Interpretation of mueller matrices based on polar decomposition," Journal of the Optical Society of America A, May 1996, pp. 1106-1113, vol. 13, No. 5.

Gan et al., "Dispersion analysis of collagen fiber networks in cervical tissue using optical coherence tomography," Photonic Therapeutics and Diagnostics XII, May 2016, vol. 9689, Abstract.

Garfield et al., "Methods and devices for the management of term and preterm labor," Annals of the New York Academy of Sciences, Sep. 2001, pp. 203-224, vol. 943.

Pierangelo et al., "Polarimetric imaging of uterine cervix: a case study," Optics Express, Jun. 5, 2013, pp. 14120-14130, vol. 21, No. 12.

Bai et al., "Dynamic multicomponent engineered tissue reorganization and matrix deposition measured with an integrated nonlinear optical microscopy-optical coherence microscopy system," Journal of Biomedical Optics, Mar. 2014, pp. 036014-1-036014-10, vol. 19, No. 3.

Soleimani et al., "Long-term neurodevelopmental outcomes after preterm birth," Iran Red Crescent Medical Journal, Jun. 5, 2014, pp. 1-8, vol. 16, No. 6.

Saiga et al., "An overview of mortality and sequelae of preterm birth from infancy to adulthood," Lancet, Jan. 19, 2008, pp. 261-269, vol. 371.

Kemp et al., "Preterm birth, infection, and inflammation advances from the study of animal models," Reproductive Sciences, Jul. 2010, pp. 619-628, vol. 17, No. 7.

Kozuki et al., "The associations of birth intervals with small-for-gestational-age, preterm, and neonatal and infant mortality: a meta-analysis," BMC Public Health, Sep. 2013, pp. 1-9, vol. 13, No. 3.

Tielsch et al., "Global Incidence of preterm birth," Low-Birthweight Baby: Born Too Soon or Too Small, Nestle Nutrition Institute Workshop Series, Jun. 19, 2015, pp. 9-15, vol. 81.

Iams et al., "The length of the cervix and the risk of spontaneous premature delivery," The New England Journal of Medicine, Feb. 29, 1996, pp. 567-572, vol. 334, No. 9.

Feltovich et al., "Quantitative ultrasound assessment of cervical microstructure," Ultrasonic Imaging, Jul. 2010, pp. 131-142, vol. 32, No. 3.

Nold et al., "Inflammation promotes a cytokine response and disrupts the cervical epithelial barrier: a possible mechanism of premature cervical remodeling and preterm birth," American Journal of Obstetrics and Gynecology, Mar. 2012, pp. 1-7, vol. 206, No. 208.

Zarko et al., "Continuous cardiotocography (CTG) as a form of electronic fetal monitoring (EFM) for fetal assessment during labour," Cochrane Database of Systematic Reviews, May 2013, pp. 1-136, No. 5.

Honest et al., "Accuracy of cervicovaginal fetal fibronectin test in predicting risk of spontaneous preterm birth: systematic review," The BMJ, Aug. 2002, pp. 40-63.

Berghella et al., "Cervical assessment by ultrasound for preventing preterm delivery," Cochrane Database of Systematic Reviews, Jan. 2013, pp. 1-37, No. 1.

Zork et al., "A systematic evaluation of collagen crosslinks in the human cervix," American Journal of Obstetrics and Gynecology, Mar. 2015, pp. 1-20, vol. 212, No. 3, Author Manuscript.

Fernandez et al., "Investigating the Mechanical Function of the Cervix during Pregnancy using Finite Element Models derived from High Resolution 3D MRI," Computer Methods in Biomechanics and Biomedical Engineering, Mar. 2016, pp. 1-29, vol. 19, No. 4, Author Manuscript.

Akins et al., "Second harmonic generation imaging as a potential tool for staging pregnancy and predicting preterm birth," Journal of Biomedical Optics, Mar./Apr. 2010, pp. 026020-1-026020-10, vol. 15, No. 2.

Read et al., "Cervical remodeling during pregnancy and parturition: molecular characterization of the softening phase in mice," Reproduction, Jul. 2007, pp. 327-340, vol. 134.

Ito et al., "The change in solubility of type I collagen in human uterine cervix in pregnancy at term," Biochemical Medicine, Jun. 1979, pp. 262-270, vol. 21.

(56) References Cited

OTHER PUBLICATIONS

Canty et al., "Procollagen trafficking, processing and fibrillogenesis," Journal of Cell Science, Apr. 2005, pp. 1341-1353, vol. 118, No. 7.

Sennstrom et al., "Human cervical ripening, an inflammatory process mediated by cytokines," Molecular Human Reproduction, Apr. 2000, pp. 375-381, vol. 6, No. 4.

Osmers et al., "Glycosaminoglycans in cervical connective tissue during pregnancy and parturition," Obstetrics and Gynecology, Jan. 1993, pp. 88-92, vol. 81, No. 1.

Straach et al., "Regulation of hyaluronan expression during cervical ripening," Glycobiology, Jan. 2005, pp. 55-65, vol. 15, No. 1.

Romero et al., "The preterm parturition syndrome," BJOG: An International Journal of Obstetrics and Gynaecology, Dec. 2006, pp. 17-42, vol. 113.

Aspden, "Collagen organisation in the cervix and its relation to mechanical function," Collagen and Related Research, Mar. 1988, pp. 103-112, vol. 8.

Zhang et al., "A compact fiber-optic SHG scanning endomicroscope and its application to visualize cervical remodeling during pregnancy," Proceedings of the National Academy of Sciences, Aug. 7, 2012, pp. 12878-12883, vol. 109, No. 32.

Chen et al., "Second harmonic generation microscopy for quantitative analysis of collagen fibrillar structure," Nature Protocols, Mar. 2012, pp. 1-43, vol. 7, No. 4, Author Manuscript.

Myers et al., "Changes in the biochemical constituents and morphologic appearance of the human cervical stroma during pregnancy," European Journal of Obstetrics & Gynecology and Reproductive Biology, Jan. 2009, pp. S82-S89, vol. 144S.

Nazac et al., "Optimization of picrosirius red staining protocol to determine collagen fiber orientations in vaginal and uterine cervical tissues by mueller polarized microscopy," Microscopy Research and Technique, Jun. 2015, pp. 1-8, vol. 78, No. 8.

Lee et al., "Optical diagnosis of cervical intraepithelial neoplasm (CIN) using polarization-sensitive optical coherence tomography," Optics Express, Feb. 18, 2008, pp. 2709-2719, vol. 16, No. 4.

Bancelin et al., "Determination of collagen fiber orientation in histological slides using mueller microscopy and validation by second harmonic generation imaging," Optics Express, Sep. 22, 2014, pp. 22561-22574, vol. 22, No. 19.

Collier et al., "Sources of scattering in cervical tissue: determination of the scattering coefficient by confocal microscopy," Applied Optics, Apr. 10, 2005, pp. 2072-2081, vol. 44, No. 11.

Carlson et al., "Confocal microscopy: imaging cervical precancerous lesions," Gynecologic Oncology, Dec. 2005, pp. S84-S88, vol. 99, No. 3.

Pierangelo et al., "Multispectral mueller polarimetric imaging detecting residual cancer and cancer regression after neoadjuvant treatment for colorectal carcinomas," Journal of Biomedical Optics, Apr. 2013, pp. 046014-1-046014-9, vol. 18, No. 4.

* cited by examiner

| Tissue | Classifier method | Accuracy metrics | | |
|---|---|---|---|---|
| | | MSE (%) | PSNR (dB) | SSIM (%) |
| Collagen | KNN | 85.75 | 44.47 | 87.37 |
| | KNN +[3x3] filter | 87.77 | 43.09 | 86.50 |
| | KNN +[10x10] filter | 87.84 | 43.02 | 85.62 |
| | Semantic Seg. | 89.90 | 43.72 | 93.53 |
| Elastin | KNN | 87.69 | 43.00 | 87.25 |
| | KNN +[3x3] filter | 88.67 | 43.26 | 85.95 |
| | KNN +[10x10] filter | 87.58 | 42.84 | 84.45 |
| | Semantic Seg. | 89.58 | 44.13 | 91.87 |

FIG. 10

SYSTEMS AND METHODS FOR VISUALIZING ELASTIN AND COLLAGEN IN TISSUE

GOVERNMENT SUPPORT

This invention was made with government support under DMR 1548924 awarded by the National Science Foundation (NSF). The government has certain rights in the invention.

BACKGROUND

Preterm birth (PTB), defined as any birth prior to 37 completed weeks of gestation, is responsible for 35% of the annual 3.1 million global neonatal deaths. Many survivors will face life-long challenges including neurological disorders, long-term cognitive impairment, respiratory disease, and/or defects in hearing, vision, and/or digestion.

Unfortunately, there is an absence of clinical tools for early and accurate detection of spontaneous PTB risk, in part due to a lack in understanding of the molecular events that drive a term or PTB. Understanding the cervical remodeling process in a term or preterm pregnancy is critical to define therapeutic targets and to develop clinical tools.

BRIEF SUMMARY

Embodiments of the subject invention provide novel and advantageous systems and methods for visualizing, and/or determining the amount of, collagen and elastin in tissue (e.g., in thin tissue slices). Mueller matrix microscopy and machine learning approaches can be utilized; training data can be generated using Mueller matrix polarimetry microscopy data, combined with second harmonic generation (SHG) and/or two photon excitation fluorescence (TPEF) microscopy data as ground truth. The SHG and/or TPEF data can be used to train a neural network (e.g., a convolutional neural network (CNN)) for feature extraction, and classification (e.g., via K-nearest neighbor (K-NN) classification) can be performed. The components and decompositions of the Mueller matrix data can be arranged as individual channels of information, forming one voxel (e.g., four dimensional (4D) voxel) per sample. One or more classification algorithms can analyze each voxel and determine the amount of collagen and elastin, pixel by pixel, on each sample, where SHG and/or TPEF are used as ground truth.

In an embodiment, a system for visualizing elastin and collagen in tissue (e.g., cervical tissue, such as cervical tissue of a mammal (for example, a human or a mouse)) can comprise a processor and a (non-transitory) machine-readable medium in operable communication with the processor and having instructions stored thereon that, when executed by the processor, perform the following steps: receiving imaging data of the tissue; extracting from the imaging data a ground truth for collagen in the tissue and a ground truth for elastin in the tissue; extracting Mueller matrix data from the imaging data to generate a voxel of the imaging data; utilizing a neural network on the voxel to extract features and generate a feature matrix of the imaging data; and applying at least one classifier to the feature matrix to generate a predicted image to visualize the elastin and the collagen in the tissue. The instructions when executed can further perform the following step(s): before utilizing the neural network, training the neural network using the ground truth for collagen, the ground truth for elastin, and the voxel; and/or before applying the at least one classifier, training the at least one classifier using the ground truth for collagen and the ground truth for elastin. The instructions when executed can further perform the following steps: transforming the ground truth for collagen and the ground truth for elastin into a ground truth vector; before utilizing the neural network, training the neural network using the ground truth vector and the voxel; and before applying the at least one classifier, training the at least one classifier using the ground truth vector. The at least one classifier can comprise a machine vision classifier. The at least one classifier can comprise, for example, a K-NN classifier and a semantic segmentation neural network. The neural network can be, for example, a CNN. The instructions when executed can further perform the following step: comparing the visualized elastin and collagen in the tissue to the ground truth for collagen and the ground truth for elastin, using at least one of mean square error (MSE), peak signal-to-noise ratio (PSNR), and structural similarity (SSIM). The extracting of the ground truth for collagen and the ground truth for elastin can comprise using SHG and/or TPEF. For example, the SHG can be used to extract the ground truth for collagen, and the TPEF can be used to extract the ground truth for elastin. The instructions when executed can further perform the following step: before utilizing the neural network and before applying the at least one classifier, removing outliers from the voxel, the ground truth for collagen, and/or the ground truth for elastin; and/or before utilizing the neural network and before applying the at least one classifier (but after removing the outliers, if applicable), normalizing the voxel, the ground truth for collagen, and/or the ground truth for elastin. The voxel can comprise data channels, and the data channels of the voxel can respectively comprise diattenuation of the Mueller matrix data, depolarization coefficient of the Mueller matrix data, linear retardation of the Mueller matrix data, differential diattenuation of the Mueller matrix data, orientation of the Mueller matrix data, differential depolarization of the Mueller matrix data, and/or all Muller Matrix elements of the Mueller matrix data except $M_{22}$, $M_{33}$, and $M_{44}$. The imaging data can be obtained from a sample data file and/or by directly imaging the tissue (e.g., via microscopy (for example, with a microscope that is part of the system and is in operable communication with the processor and/or the machine-readable medium)).

In another embodiment, a method for visualizing elastin and collagen in tissue can comprise: receiving (e.g., by a processor) imaging data of the tissue; extracting (e.g., by the processor) from the imaging data a ground truth for collagen in the tissue and a ground truth for elastin in the tissue; extracting (e.g., by the processor) Mueller matrix data from the imaging data to generate a voxel of the imaging data; utilizing (e.g., by the processor) a neural network on the voxel to extract features and generate a feature matrix of the imaging data; and applying (e.g., by the processor) at least one classifier to the feature matrix to generate a predicted image to visualize the elastin and the collagen in the tissue. The method can further comprise: transforming (e.g., by the processor) the ground truth for collagen and the ground truth for elastin into a ground truth vector; before utilizing the neural network, training (e.g., by the processor) the neural network using the ground truth vector and the voxel; and/or before applying the at least one classifier, training (e.g., by the processor) the at least one classifier using the ground truth vector. The at least one classifier can comprise a machine vision classifier. The at least one classifier can comprise, for example, a K-NN classifier and a semantic segmentation neural network. The neural network can be, for example, a CNN. The method can further comprise comparing (e.g., by the processor) the visualized elastin and collagen in the tissue to the ground truth for collagen and the ground truth for elastin, using at least one of mean square error (MSE), peak signal-to-noise ratio (PSNR), and structural similarity (SSIM). The extracting of the ground truth for collagen and the ground truth for elastin can comprise using SHG and/or TPEF. For example, the SHG can be used to extract the ground truth for collagen, and the TPEF can be used to extract the ground truth for elastin. The method can further comprise: before utilizing the neural network and before applying the at least one classifier, removing (e.g., by the processor) outliers from the voxel, the ground truth for collagen, and/or the ground truth for elastin; and/or before utilizing the neural network and before applying the at least one classifier (but after removing the outliers, if applicable), normalizing (e.g., by the processor) the voxel, the ground truth for collagen, and/or the ground truth for elastin. The voxel can comprise data channels, and the data channels of the voxel can respectively comprise diattenuation of the Mueller matrix data, depolarization coefficient of the Mueller matrix data, linear retardation of the Mueller matrix data, differential diattenuation of the Mueller matrix data, orientation of the Mueller matrix data, differential depolarization of the Mueller matrix data, and/or all Muller Matrix elements of the Mueller matrix data except $M_{22}$, $M_{33}$, and $M_{44}$. The imaging data can be obtained from a sample data file and/or by directly imaging the tissue (e.g., via microscopy (for example, with a microscope that is in operable communication with the processor)).

BRIEF DESCRIPTION OF DRAWINGS

FIG. 4(a) shows collagen ground truth (SHG); FIG. 4(b) shows elastin ground truth (TPEF); and FIG. 4(c) shows total reflectance intensity $M_{11}$.

FIG. 10 shows a table with the accuracy of K-NN and semantic segmentation classifiers based on three metrics—mean square error (MSE, in percentage (%)), peak signal-to-noise ratio (PSNR, in decibels (dB)), and structural similarity (SSIM, in %). Results are presented for K-NN predicted images, K-NN predicted images with a median filter [3×3] applied, K-NN predicted images with a median filter [10×10] applied, and semantic segmentation predicted images, for each of collagen and elastin.

DETAILED DESCRIPTION

Figures 1A, 1B, 1C, 1D, 1E, 1F:
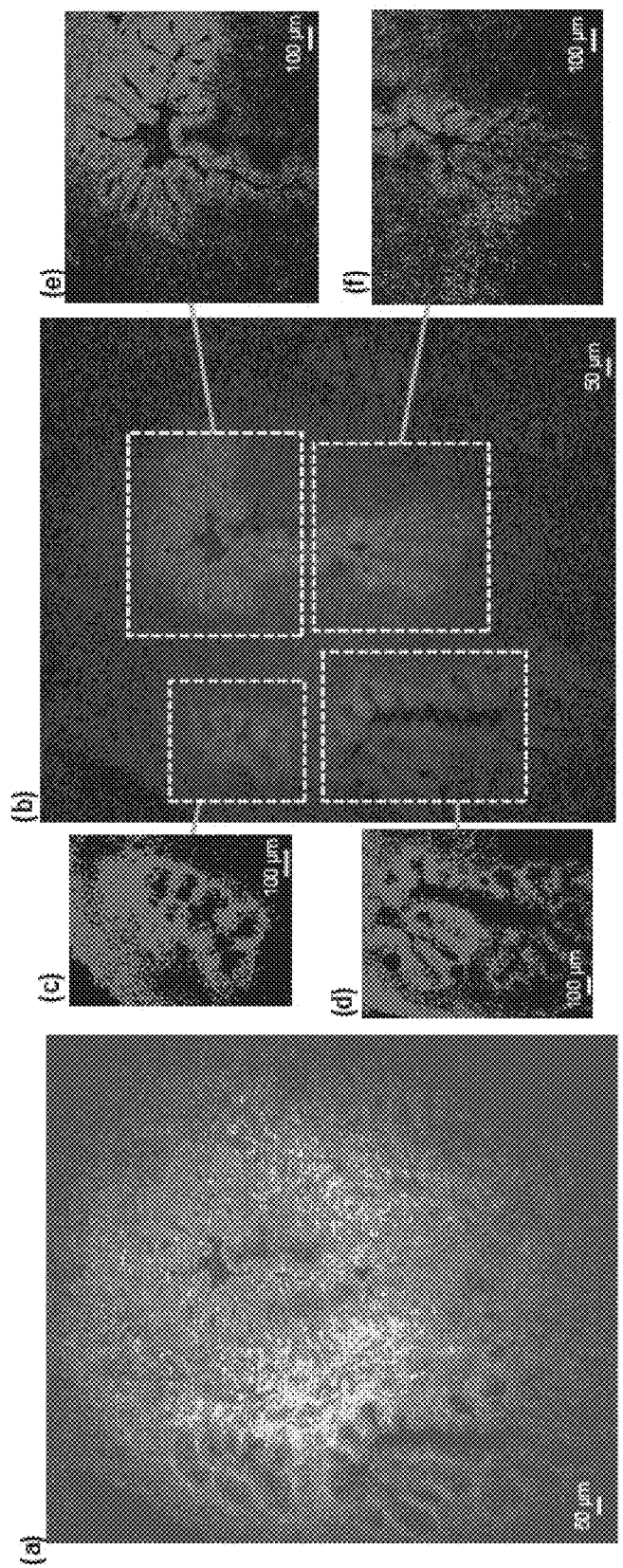
FIG. 1(a) shows a second harmonic generation (SHG) immunofluorescent image of an unstained mouse cervix at day 18 of pregnancy using a self-validating Mueller matrix micro-mesoscope (SAMMM). The scale bar is 50 The SHG signal of elastin is strong around the cervical midstroma.
FIG. 1(b) shows a two photon excitation fluorescence (TPEF) immunofluorescent image of an unstained mouse cervix at day 18 of pregnancy using a SAMMM. The scale bar is 50 µm. The immunofluorescence confirms elastin on the TPEF image. The TPEF signal of elastin is strong around the cervical OS (opening).
FIG. 1(c) shows an immunofluorescent image of a section of FIG. 1(b) (see the dotted square to which FIG. 1(c) is pointing), taken using commercial linear microscopy. The scale bar is 100 µm.
FIG. 1(d) shows an immunofluorescent image of a section of FIG. 1(b) (see the dotted square to which FIG. 1(d) is pointing), taken using commercial linear microscopy. The scale bar is 100 µm.
FIG. 1(e) shows an immunofluorescent image of a section of FIG. 1(b) (see the dotted square to which FIG. 1(e) is pointing), taken using commercial linear microscopy. The scale bar is 100 µm.
FIG. 1(f) shows an immunofluorescent image of a section of FIG. 1(b) (see the dotted square to which FIG. 1(f) is pointing), taken using commercial linear microscopy. The scale bar is 100 µm.

Embodiments of the subject invention provide novel and advantageous systems and methods for visualizing, and/or determining the amount of, collagen and elastin in tissue (e.g., in thin tissue slices). Mueller matrix microscopy and machine learning approaches can be utilized; training data can be generated using Mueller matrix polarimetry microscopy data, combined with second harmonic generation (SHG) and/or two photon excitation fluorescence (TPEF) microscopy data as ground truth. The SHG and/or TPEF data can be used to train a neural network (e.g., a convolutional neural network (CNN)) for feature extraction, and classification (e.g., via K-nearest neighbor (K-NN) classification) can be performed. The components and decompositions of the Mueller matrix data can be arranged as individual channels of information, forming one voxel (e.g., four dimensional (4D) voxel) per sample. One or more classification algorithms can analyze each voxel and determine the amount of collagen and elastin, pixel by pixel, on each sample, where SHG and/or TPEF are used as ground truth.

Given the reorganization of the cervical extracellular matrix (ECM) through pregnancy and its direct correlation with mechanical function of the cervix, embodiments of the subject invention aim to provide improved methodology to characterize collagen and elastin fibers (e.g., in a cervix, such as a cervix of a mammal (for example, a mouse or a human)).

An ECM lies under the epithelium of the cervix and includes about 70% collagen fibers. Cervical collagen and its anisotropic alignment surrounding the cervical canal can be examined through SHG and transmission electron microscopy (TEM). Collagen is the main load bearing component of the cervical stroma, which undergoes substantial remodeling during pregnancy. Collagen molecules are organized into fibrils through enzymatic cross-links. Mature cross-link density can decrease substantially in a mouse model between day 12 and day 18 of gestation, resulting in increased collagen solubility and reduced tissue stiffness as pregnancy progresses.

Elastic fibers are also important components of the cervix ECM and includes elastin polymer cross-linked into microfibrils. In the cervix, elastin fibers are intertwined with collagen fibers and are primarily located in the subepithelial stroma. Elastic fibers are modified during pregnancy, becoming more dispersed and less ordered. While not well studied at the molecular level, a reduction in cross-link density of elastic fibers is correlated with preterm birth due to cervical insufficiency. Assessment of elastin is complicated by its paucity compared to collagen in the cervix. TPEF, TEM, and fluorescence confocal microscopy with immunofluorescence are among the most effective modalities for elastin assessment in the cervical environment.

Polarization-based microscopy techniques enhanced by Sirius red staining can offer similar imaging capability of cervical collagen as that of SHG-based modalities. Mueller matrix polarimetry can also be used to image the cervix and its collagen arrangement. No related art systems or methods use polarization optical modalities in the assessment of the cervical elastic fibers. The use of the Mueller matrix modality, which does not require complex instrumentation or specialized staining, can accelerate the development of clinical tools for assessment of cervical function and risk of malfunction. Embodiments can utilize Mueller matrix microscopy and machine learning. For example, a self-validating Mueller matrix micro-mesoscope (SAMMM) can be used for the characterization of collagen and/or elastin fibers (e.g., in a cervix, such as a cervix of a mammal (for example, a mouse or a human)).

Machine learning can aid greatly in analyzing and diagnosing large numbers of samples. Many classification methods that have been applied to Muller matrix imaging previously have not been used to visually separate elastin from collagen (e.g., in a cervix). Embodiments of the subject invention can utilize a K-NN algorithm (e.g., a supervised K-NN algorithm) and/or a neural network (e.g., a deep learning semantic segmentation neural network) to detect and classify collagen and elastin fibers, based on the Muller matrix components. A supervised (K-NN) algorithm can be used to associate pixels with similar characteristics into defined groups using the Muller matrix components as features. A deep learning semantic segmentation neural network can be used to assign pixels into different layers depending on their intensity. Deep learning segmentation is used in biomedical imaging for a wide variety of diagnostics. Such networks typically have higher accuracy and are more robust than other classifiers but require more time and samples for training. In order to reduce training time, a knowledge transfer from a well-tested CNN (e.g., Resnet18) can be used.

Related art systems and methods to differentiate collagen from elastin in tissue use non-linear microscopy (NLM) and histological staining. NLM systems are very costly and require trained personnel to operate while histology can be used to visualize both collagen (Sirius red) and elastin (using rabbit anti-mouse tropoelastin antibody as the primary antibody and Alexa Fluor 546-conjugated antibodies the secondary antibody), but these approaches are laborious and require specialized knowledge. In contrast, systems and methods of embodiments of the subject invention utilize Mueller matrix polarimetry, which can be implemented on a standard microscope, and the machine learning algorithm can provide a virtual stain of the measured sample. That is, embodiments provide ease of use and affordability.

In certain embodiments, reflectance measurements of SHG, TPEF, and near-infrared total reflectance images can be performed using a SAMMM system (see also Du Le et al., Depth-resolved Mueller matrix polarimetry microscopy of the rat cornea, Biomed Opt Express 11, 5982-5994, 2020; and Saytashev et al., Self validating Mueller matrix Micro-Mesoscope (SAMMM) for the characterization of biological media, Opt Lett 45, 2168-2171, 2020; both of which are hereby incorporated herein by reference in their entireties).

The Mueller matrix M of a medium can be decomposed using the Lu-Chipman decomposition method in which M can be expressed as the product of three basic matrices (see also Lu et al., Interpretation of Mueller matrices based on polar decomposition, J Opt Soc Am A 13, 1106-1113, 1996; which is hereby incorporated herein by reference in its entirety):

$$M = M_\Delta M_R M_D \tag{1}$$

where $M_\Delta$, $M_R$, and $M_D$ are depolarization Mueller matrix, retardance Mueller matrix, and diattenuation Mueller matrix, respectively. Following the decomposition, scalar terms such as diattenuation (d), depolarization coefficient ($\Delta$), linear retardation ($\delta$) of the medium can be determined:

$$d = \frac{\sqrt{M_D^2(1,2) + M_D^2(1,3) + M_D^2(1,4)}}{M_D(1,1)} \tag{2}$$

$$\Delta = 1 - \frac{|M_\Delta^T - 1|}{3} \tag{3}$$

$$\delta = \cos^{-1}\left(\sqrt{(M_R^2(2,2) + M_R^2(3,3))^2 + (M_R^2(3,2) - M_R^2(2,3))^2} - 1\right) \tag{4}$$

In addition to polar decomposition, differential matrix formalism of the Mueller calculus can be used to retrieve total retardance (linear and circular) (see also Qi et al., Mueller polarimetric imaging for surgical and diagnostic applications: a review, J Biophotonics 10, 950-982, 2017; which is hereby incorporated herein by reference in its entirety). In this case, the medium polarization properties are contained in a single differential matrix m, which relates the Mueller matrix M and its spatial derivative along the propagation of light (see also Azzam, Propagation of Partially Polarized-Light through Anisotropic Media with or without Depolarization—Differential 4×4 Matrix Calculus, J Opt Soc Am 68, 1756-1767, 1978; and Ortega-Quijano et al., Mueller matrix differential decomposition, Optics Letters 36, 1942-1944, 2011; which are hereby incorporated herein by reference in their entireties):

$$\frac{dM}{dz} = mM \quad (5)$$

Applying Lorentz symmetric matrices, $L_m$ and Lorentz antisymmetric matrices, $L_u$ to Equation (5), the following is obtained:

$$\ln M = mz = L = L_u + L_m \quad (6)$$

where $$L_m = \frac{1}{2}(L - GL^T G) \quad (7)$$

$$L_u = \frac{1}{2}(L + GL^T G) \quad (8)$$

In Equations (7) and (8), G is the Minkowski metric tensor. For a depolarizing medium, the off-diagonal elements of $L_m$ represent mean values of the elementary medium polarization properties over the path-length z, and the off-diagonal elements of $L_u$ express their respective uncertainties. Lorentz components of the matrices can be used to retrieve both linear ($\delta_L$), circular ($\delta_C$), and total (R) retardation, diattenuation (d), depolarization (Δ), angle of orientation (θ):

$$\delta_C = \frac{L_m(2,3)}{2} \quad (9)$$

$$\delta_L = \sqrt{(L_m(2,4))^2 + (L_m(3,4))^2} \quad (10)$$

$$R = \sqrt{\delta_L^2 + 4\delta_C^2} \quad (11)$$

$$d = \tanh\sqrt{(L_m(1,2))^2 + (L_m(1,3))^2 + (L_m(1,4))^2} \quad (12)$$

$$\Delta = \frac{|L_u(2,2) - L_u(1,1)| + |L_u(3,3) - L_u(1,1)| + |L_u(4,4) - L_u(1,1)|}{3} \quad (13)$$

$$\theta = \frac{1}{2}\tan^{-1}\frac{\{L_m(2,4)\}}{\{L_m(3,4)\}} \quad (14)$$

While SHG of collagen in the cervix is optimal at a wavelength in the region of 400 nm or about 400 nm with the excitation at 800 nm (see also FIG. 1(a)), elastin and reduced nicotinamide adenine dinucleotide (NADH) have an overlapping fluorescence emission in the region of 500 nm or about 500 nm. Other glycosaminoglycans (GAGs) and proteoglycans could also contribute to the TPEF signal. Therefore, in order to confirm that cervical elastin is responsible for TPEF signal in the samples, indirect immunofluorescence of one or more selected samples can be performed.

Figure 2:
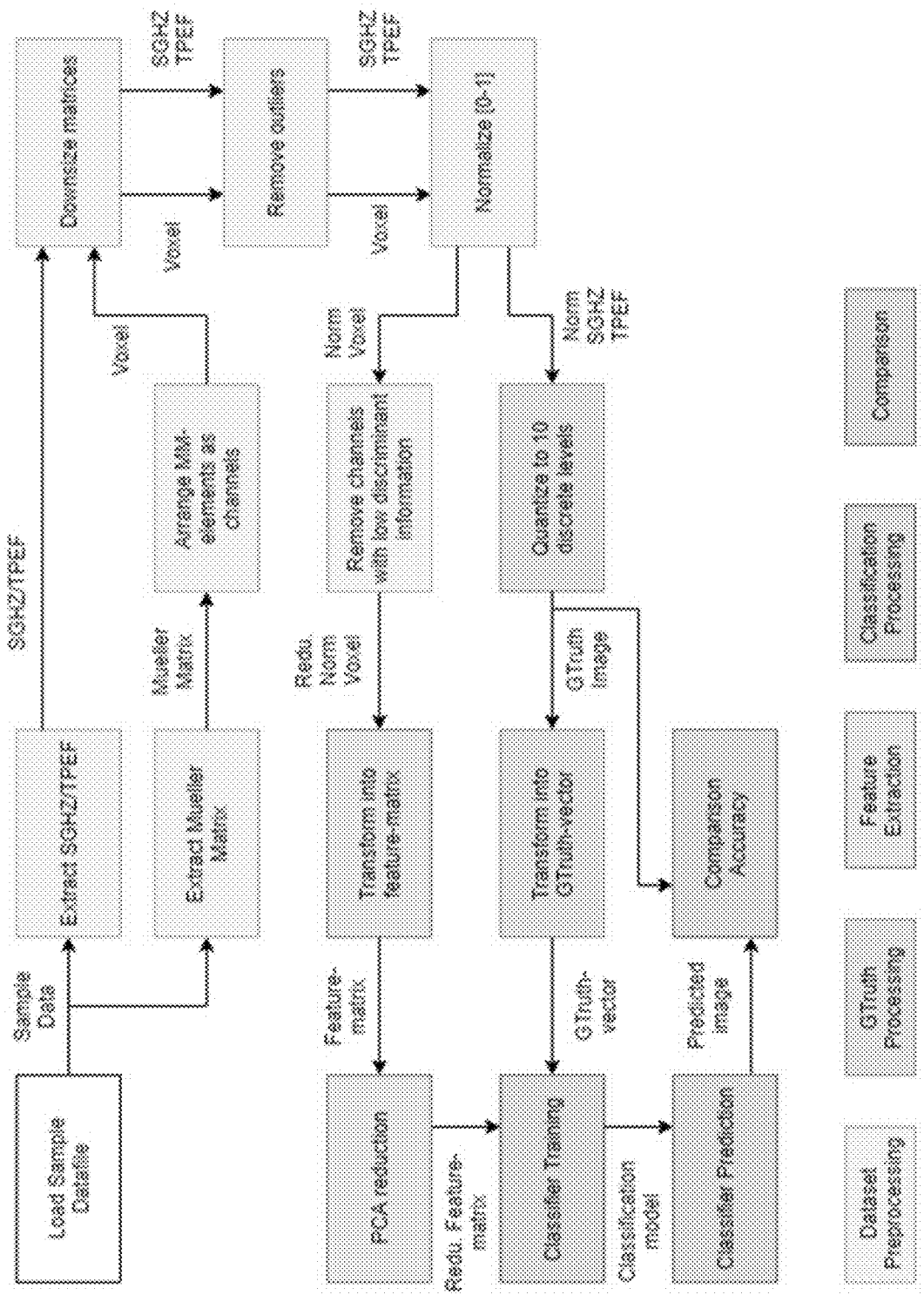
FIG. 2 shows a block diagram of an algorithm to detect and classify collagen and/or elastin in a sample, according to an embodiment of the subject invention.

In embodiments, an algorithm can be used to process and classify the data by applying it to the Muller matrix data and its decompositions. FIG. 2 shows a block diagram of such an algorithm. The process can extract the ground truth, normalize the samples, extract features, apply at least one classification methodology (e.g., two classification methodologies), and/or compare the results for accuracy. For example, the classification methodologies can be machine vision classifiers, such as K-NN and a semantic segmentation neural network. Neural networks are especially useful for imaging diagnostics.

For each data sample, the corresponding SHG and TPEF can be obtained. SHG data can be set as the ground truth of collagen while TPEF can be set as the ground truth of elastin. Each ground truth can be represented by one image in which the intensity is related with the density of it respective tissue.

Figure 3:
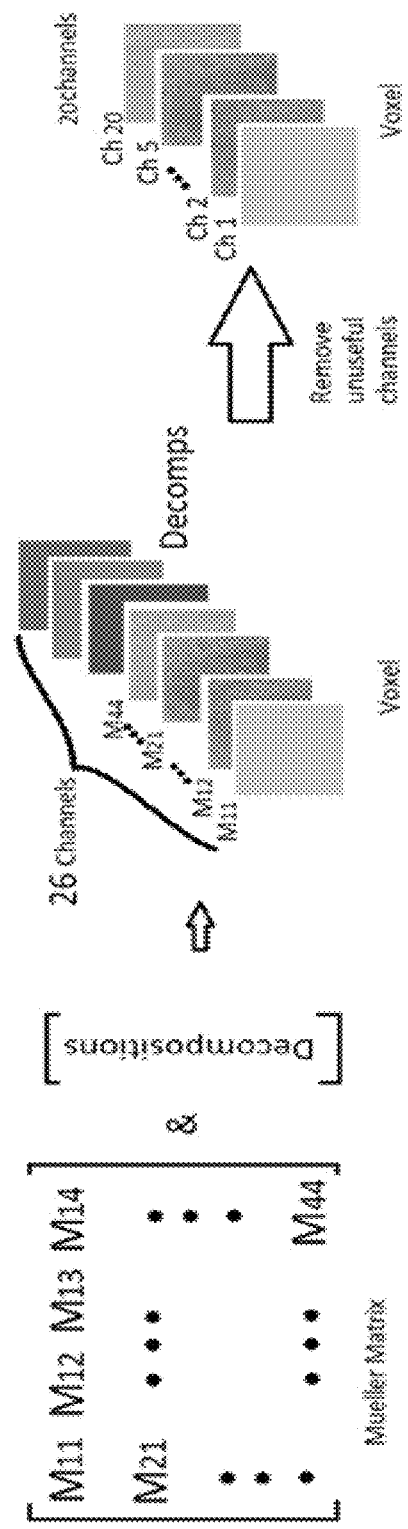
FIG. 3 shows a diagram of transitioning from a Mueller matrix and decompositions to a voxel with data channels, according to an embodiment of the subject invention.

The Muller matrix elements ($M_{11}, M_{12}, \ldots, M_{44}$) of data samples, along with the decomposition values of the Mueller matrix, can be arranged as a voxel where the channels of information correspond to the matrix's elements or the decompositions. All elements and decompositions can be aligned so a specific pixel has 26 initial channels (layers) of information. Some of the voxel's channels may not bring useful discriminating information. Channels with very low standard deviation can be removed because they are mostly noise. Additionally, information on some channels may be very similar to others, so redundant channels can also be removed after comparing them with each other (e.g., using a structural similarity index (see also Zhou et al., Image quality assessment: from error visibility to structural similarity, IEEE Transactions on Image Processing 13, 600-612, 2004; which is hereby incorporated by reference herein in its entirety). FIG. 3 shows a diagram of this process. The following variables can be used as data channels of the voxel: diattenuation (see Equation (2)), depolarization coefficient (see Equation (3)), linear retardation (see Equation (4)), differential diattenuation (see Equation (12)), orientation (see Equation (14)), differential depolarization (see Equation (13)), and all Muller Matrix elements except $M_{22}$, $M_{33}$, and $M_{44}$.

SHG, TPEF, and data voxels can optionally be reduced (e.g., to 0.4 (or 40%) of original size) so the computation is more efficient. Due to errors in the sampling process or data gathering, outlier pixels may be present. Pixels with very high values compared to their neighbors can skew the classification process. Thus, outliers can be removed from the voxel, the SHG, and the TPEF data (e.g., using the Grubbs method). The outlier pixels can be replaced by the mean of their neighbors. A standard normalization (based on the maximum and minimum of the sample) of SHG, TPEF, and each channel of the voxel can be applied, so they are comparable among each other. The value of any pixel is in between 0 and 1.

Figures 4A, 4B, 4C:
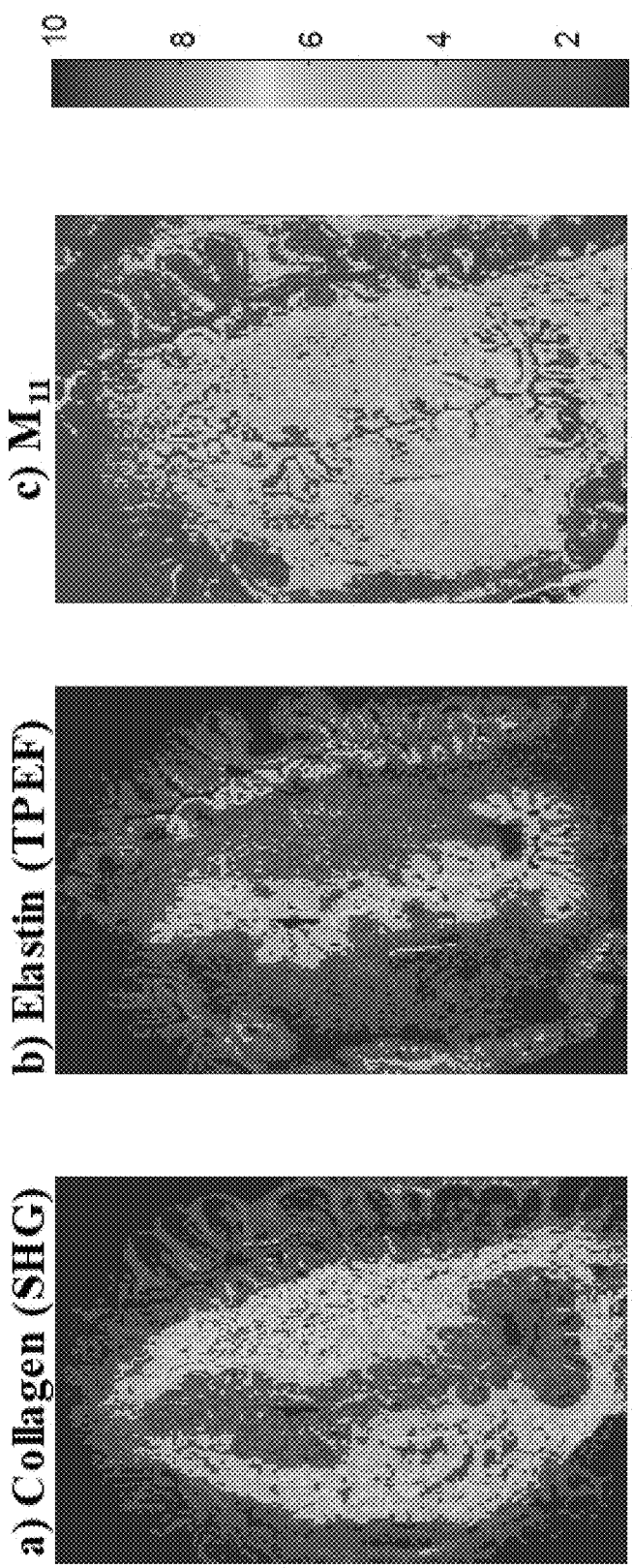
FIGS. 4(a)-4(c) show a cervical cross-section from a gestation day 18 mouse, with 10-level images with densities represented on a heat scale (to the right of FIG. 4(c)).

The normalized SHG and TPEF can be converted into 10 discrete levels to obtain a ground truth appropriate for classification (see also FIGS. 4(a)-4(c)). All values of SHG and TPEF can be rounded to one of those discrete values. The intensity of a pixel can be associated with the density of collagen or elastin in an area; the higher the level, the denser the collagen or elastin.

Figure 5:
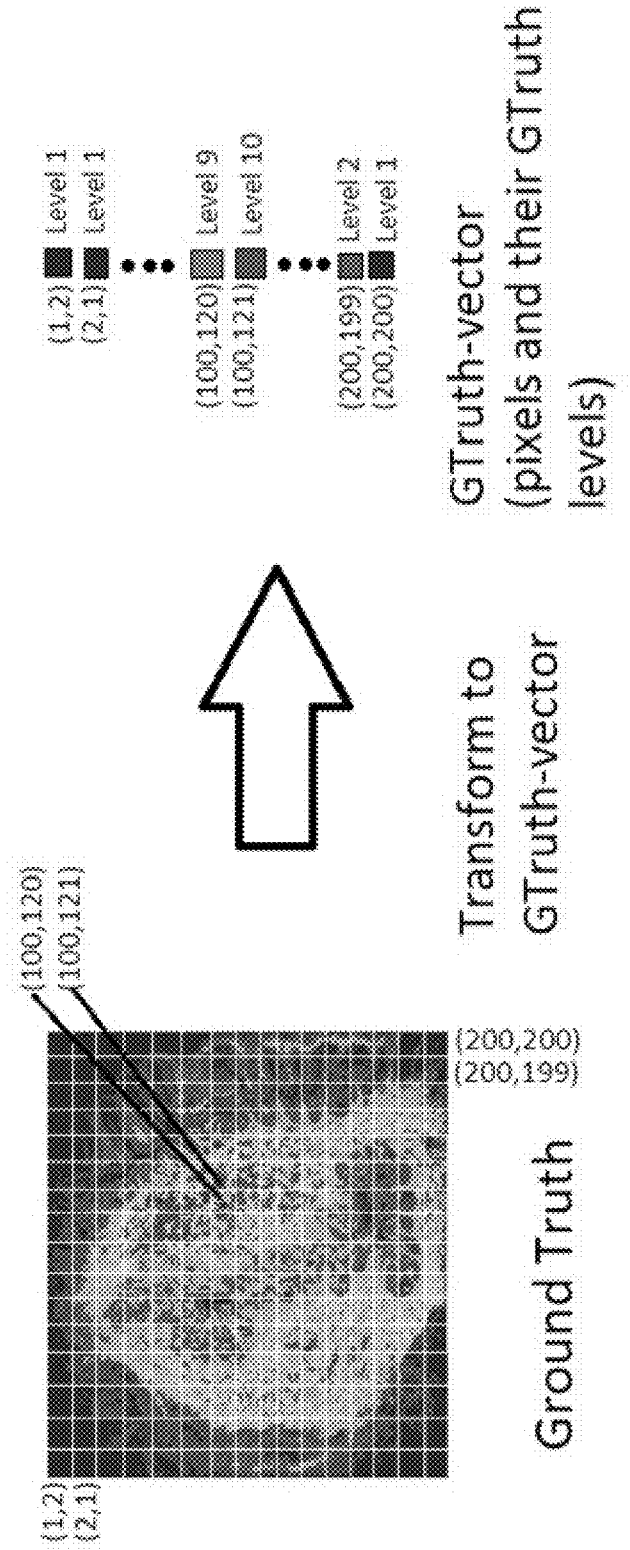
FIG. 5 shows a diagram of transforming a ground truth image to a GTruth-vector, according to an embodiment of the subject invention. Transformation for a collagen data sample is depicted, though this is for exemplary purposes only.

For the K-NN case, the ground truth image can be arranged as a vector of GTruth levels, and the vector position's index can be associated with the position of a pixel in the GTruth image (see FIG. 5). For the semantic segmentation case, each level of the ground truth can act as a layer superimposed on the sample data. The ground truth is an image of the same size as the input data with categorical values (levels) for each pixel, so it is, in essence, equal to the ground truth of the K-NN classifier.

Figure 6:
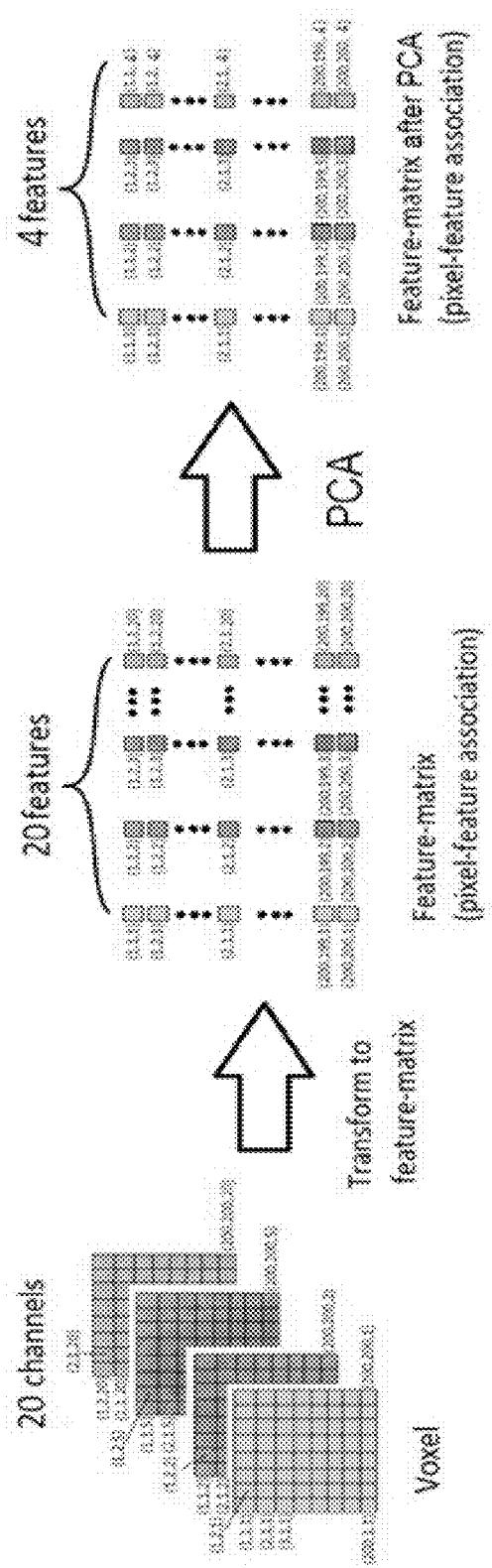
FIG. 6 shows a diagram of transforming a voxel to a feature-matrix for a K-nearest neighbor (K-NN) classifier.

K-NN classifiers take several observations and try to group them together based on the similarity of their features. Standard input for a K-NN classifier is a single matrix in which the rows represent independent observations and the columns are features associated with those observations. Referring to FIG. 6, the voxel can be arranged into a matrix of features where a row of the matrix is linked to a pixel and the columns are its corresponding channels/features. The number of features can be further reduced using principle component analysis (PCA). The size of the features can be decreased to 4 or approximately 4 by taking the features that compose 95% of the discrimination information.

For the semantic segmentation classifier, data channels can be reduced to only linear retardation and Muller matrix elements $M_{34}$ and $M_{43}$, because these can be the most dissimilar among each other and they can carry more discriminant information than other channels. They can be treated as red-green-blue (R-G-B) components of an image. Features can be extracted based on a neural network (e.g., a CNN), which can be pretrained (e.g., a pretrained CNN Resnet18). K-NN methodology does not increase the number of features, using only the remaining Muller matrix components. On the other hand, semantic segmentation algorithm takes those remaining components and extracts thousands of features.

A five-neighbors K-NN classifier can be trained based on collagen and elastin ground truths and a matrix of features. Typically, 70% of the rows on the matrix are used for training and the remaining 30% are left for testing. The training algorithm can produce a model of the classifier that is used later as a detector when new features are presented. In order to save computational time and reduce the amount of training data in the semantic segmentation case, transfer information from a pre-trained CNN into a semantic segmentation network can be used. Two networks (e.g., Deep-Lab v3+ networks), based on the semantic segmentation network, can be trained interpedently with a set of samples of collagen and a set of samples of elastin, respectively (e.g., with 11 samples of collagen and 11 of elastin, respectively). The networks can use encoder-decoder architectures, dilated convolutions, and/or skip connections to segment images. Data can be artificially augmented to increase the number of samples, and/or random left/right reflection and/or random X/Y translation of +/−10 pixels can be applied.

The two classifying methodologies can be applied to each of the samples. Intensity levels from 1-10 can be used to represent the amount of tissue predicted, with 1 being a low amount and 10 being a high amount. The output of the K-NN model is a predicted pixel-level image of the same dimensions as the original inputs, where classification errors on the predicted image are seen as static noise (salt and pepper noise). A filter that calculates the median of the neighborhood around each pixel can be used to smooth the noise on the K-NN prediction. The image is more or less granular depending on the size of the filtering window. For example, a window size of [3×3] pixels or [10×10] pixels can be used. The semantic segmentation methodology produces two independent predictions, based on the collagen and elastin fiber network, where the outputs are images (masks) of the same size as the input.

The original ground truth and the predicted image can be compared for measuring image quality, for example using different methods. For example, mean-squared error (MSE), peak signal-to-noise ratio (PSNR), and/or structural similarity (SSIM) index can be used for comparison.

Embodiments of the subject invention provide methodology for cervical collagen and elastin assessment that integrates Mueller matrix polarimetry, CNN for feature extraction, and K-NN for classification.

Original digitalized samples have a large size than can cause a significant increase in computing time, especially for K-NN classifiers. Embodiments of the subject invention can reduce the size of such images (e.g., to 200×200 pixels) without sacrificing accuracy. The reduction makes processing, training, and classification more manageable. Some Muller matrix components or decompositions do not provide relevant classification information (e.g., depolarization with differential method, total retardation, and Muller Matrix components $M_{22}$, $M_{33}$, and $M_{44}$). Simple feature reduction techniques (e.g., average standard deviation or PCA) can reduce the components used and the size of the samples with no (or limited) negative effect on the accuracy. The K-NN model is quick to train but significantly slower in making predictions compared to semantic segmentation, while semantic segmentation takes substantially more time to train but is very fast in predicting. Depending on the problem, each method can be used independently to mutually confirm their results.

The use of SHG and TPEF images as ground truths is effective in embodiments of the subject invention. While outlier pixels from the initial sampling process can skew the quantization and introduce error to the classification, outliers can be removed during the process. All images can be normalized locally and, because the raw values among samples vary greatly, this may affect the elastin samples more. The ratio of high-level pixels to low-level pixels is very small, even after normalization, which represents a bias towards low-level pixel detections.

Predicted collagen images can have greater similarity to the ground truth than do elastic fiber images when considering cervical tissue. This is in part because there is more collagen protein than elastin in the samples, rendering more pixels with higher concentration associated with collagen than those associated with elastin. In addition, collagen structures occupy a larger area making them easier to detect. However, accuracies for both components, based on independently detecting collagen or elastin on the same sample, are comparable. Each pixel of a sample can have a collagen and an elastin level associated after classification; those levels are not mutually exclusive and sometimes overlap. That means that there could be a discrepancy on the classification, which would need a joint classification approach (collagen and elastin at the same time), or it could mean that both tissues are present at the same time because collagen and elastin tissues are frequently intertwined. This is a limitation of independently classifying collagen and elastic fibers.

Measuring image quality is difficult because some metrics do not match subjective perception. Further, the number of pixels representing collagen or elastin is significantly smaller compared to the "background", pixels which is why some accuracy metrics are relatively high, but the ground truth and predicted images do not look that similar in the example. The classifiers are good at detecting the low-intensity "background" pixels, which make up the majority, but they are not as good at properly classifying high-intensity pixels. Estimating the exact number of samples needed to successfully train a neural network is very difficult if not impossible. The minimum number of samples depends directly on the characteristics of the problem and the chosen network (e.g., CNN) architecture. In some embodiments, the minimum number of samples for training can be 20, 30, 40, 50, 100, 150, 200, 250, 300, 350, 400, 450, 500, 1000, 1500, 2000, 2500, 3000, 3500, 4000, 5000, 6000, or more.

Embodiments of the subject invention can use Mueller matrix microscopy and machine learning approaches. Mueller matrix microscopy presents several advantages compared to other modalities used for the quantification of collagen and elastin such as NLM or SHG (on its own). The modality is relatively low cost, easy to use, fast, and can be designed with low encumbrance. Combined with machine learning approaches, this modality can expand the toolkit of researchers studying the reproductive system and particularly preterm labor. Training of the system with SHG and TPEF is performed, but beyond the training phase, classification of elastin and collagen (e.g., cervical elastin and collagen) can be achieved through a Mueller matrix system alone.

Embodiments of the subject invention address the technical problem of determining or visualizing the amount of collagen and elastin in tissue (e.g., cervical tissue) by providing the technical solution of combining Mueller matrix microscopy and machine learning approaches to provide ease of use and affordability in visualizing the amount of collagen and elastin in tissue, thereby increasing the chances of early and accurate detection of spontaneous preterm birth risk.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Cervical samples from two pregnant mice were obtained at day 6 (D6, N=8 slides) and day 18 (D18, N=8 slides) of pregnancy in accordance with the Institutional Animal Care and Use Committee protocol. The tissue was snapped frozen at −80° C. in optimal cutting temperature (OCT) compound (Tissue Tek, Elkhart, Ind.). The entire length of the cervix was cryosectioned transversely at −20° C. using a cryostat (Leica CM3050). Sections were mounted in on glass slides, and left to dry for 1 hour at room temperature. Unwanted residues were washed away with phosphate buffered saline (PBS).

Reflectance measurements of SHG, TPEF, and near-infrared total reflectance images were performed using a SAMMM system (see also Du Le et al., supra., and Saytashev et al., supra.). Only the total reflectance channel was used for the experiments. The excitation source was a pre-compensated mode locked laser beam from a Ti-Sapphire broadband femtosecond laser with the central wavelength at 800 nm (full width at half maximum (FWHM)=100 nanometers (nm)). The SHG signal at 400+/−30 nm and the TPEF at 500+/−20 nm, and total reflectance images, were collected by appropriated photo-multiplier tube detectors and a single data acquisition board sampled up to 125 megahertz (MHz) (Vidrio Technologies LLC, VA). Each Mueller matrix was constructed utilizing a polarization state analyzer (PSA, of four polarization states) and a polarization state generator (PSG, of six polarization states), resulting in a set of 24 images in each of the three channels. All SAMMM raw images of the mice cervix had a resolution of 1000×1000 pixels and were taken with a 5× objective.

While SHG of collagen in the cervix is optimal at a wavelength in the region of 400 nm or about 400 nm with the excitation at 800 nm (see also FIG. 1(a)), elastin and reduced nicotinamide adenine dinucleotide (NADH) have an overlapping fluorescence emission in the region of 500 nm or about 500 nm. Other glycosaminoglycans (GAGs) and proteoglycans could also contribute to the TPEF signal. Therefore, in order to confirm that cervical elastin was responsible for TPEF signal in the tested samples, indirect immunofluorescence of a selected slide was performed using rabbit anti-mouse tropoelastin antibody (Elastin Products Company, PR385) as the primary antibody and Alexa Fluor 546-conjugated antibody (Life Technologies, A11035) as the secondary antibody. Slides were washed 20 millimolar (mM) Tris (pH=8.0) for 15 minutes followed by treating the section with 100 mM iodoacetamide (Sigma-Aldrich Inc., 15161) in the dark for 15 minutes.

Diluted goat serum at 10% (ThermoFisher Scientific, 31872) was used to block the section for 1 hour at room temperature. The section was then incubated with 1:250 dilution of primary antibody in 1% goat serum overnight at 4° C. The section was then washed with PBS and incubated in 1:500 dilution of secondary antibody in 1% goat serum for 30 minutes at room temperature. The section was imaged using a commercial linear microscope (Olympus BX61) with a laser at 550 nm and a 10× objective. As shown in FIGS. 1(a)-1(f), the TPEF signal (FIG. 1(b)) obtained with SAMMM showed strong correlation to the immunofluorescence images of elastin (FIGS. 1(c)-1(f)). TPEF images of the mice cervix in were also used as ground truth for elastin.

In order to save computational time and reduce the amount of training data in the semantic segmentation case, transfer information from a pre-trained Resnet18 into a semantic segmentation network was done. Two DeepLab v3+ networks, based on the semantic segmentation network, were trained interpendently with 11 samples of collagen and 11 of elastin, respectively. The networks used encoder-decoder architectures, dilated convolutions, and skip connections to segment images. Data was artificially augmented to increase the number of samples, and random left/right reflection and random X/Y translation of +/−10 pixels was applied.

The original ground truth and the predicted image were compared for measuring image quality, using three different methods: mean-squared error (MSE), peak signal-to-noise ratio (PSNR), and structural similarity (SSIM) index (see also Zhou et al., supra.). MSE and PSNR are purely mathematical metrics and may not agree with human perception of the image quality. SSIM considers local contrast and luminance and agrees more closely with a subjective metric.

Utilizing the MATLAB built-in function "immse.m", the MSE metric compared the data matrices of the original and predicted images, pixel by pixel, then calculated the MSE for each pixel pair, averaged them, and subtracted the value from 1. Meanwhile, the function "psnr.m" was used to find the PSNR, which indicates the ratio of the maximum pixel intensity to the power of the distortion. It compared the original and predicted images as if the classifier was a transmission system introducing noise, the original images were a transmitted signal, and the predicted images were a received signal. A high SNR (e.g., >40 dB) is considered excellent, and a low SNR (e.g., <10 dB) is considered poor. The MATLAB built-in function "ssim.m" was used to find the SSIM, which combines local image structure, luminance, and contrast into a single local quality score given as a percentage. Structures were selected as patterns of pixel intensities, particularly among neighboring pixels.

Example 1

The systems and methods of embodiments of the subject invention were tested, using the materials and methods set forth above, on a mouse cervix.

On an Intel Core i7, 3.40 GHz, with 32 GB of RAM, the K-NN model ran for five minutes to train and 30 minutes to predict a sample. Semantic segmentation took substantially more time to train (around 60 hours) but had much faster prediction time (3 seconds per sample).

Figure 7:
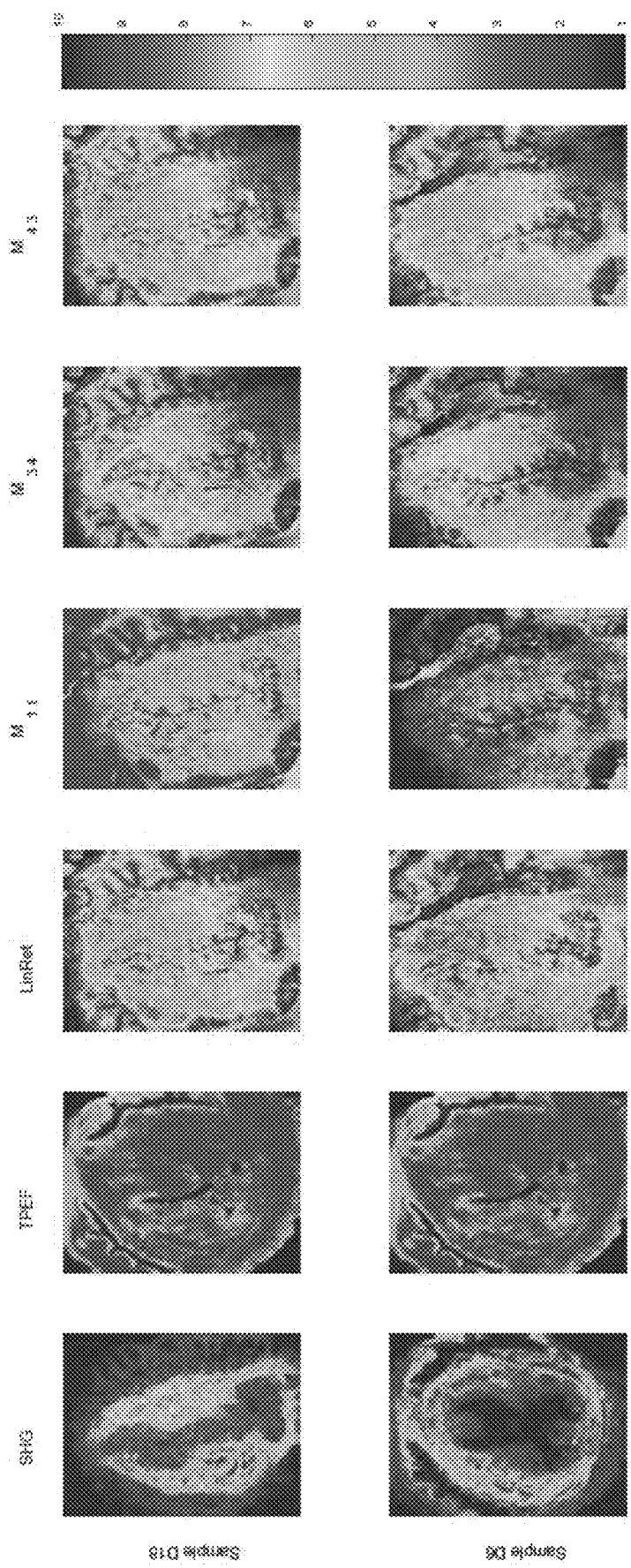
FIG. 7 shows images for ground truth (SHG) for collagen (first column, labeled "SHG"), ground truth (TPEF) for elastin (second column, labeled "TPEF"), linear retardation (third column, labeled "LinRet"), and Mueller matrix components $M_{11}$, $M_{34}$, and $M_{43}$ (fourth-sixth columns, labeled "$M_{11}$", "$M_{34}$", and "$M_{43}$", respectively), for sample D18 (first row, labeled "Sample D18") and D6 (second row (labeled "Sample D6").
Figure 8:
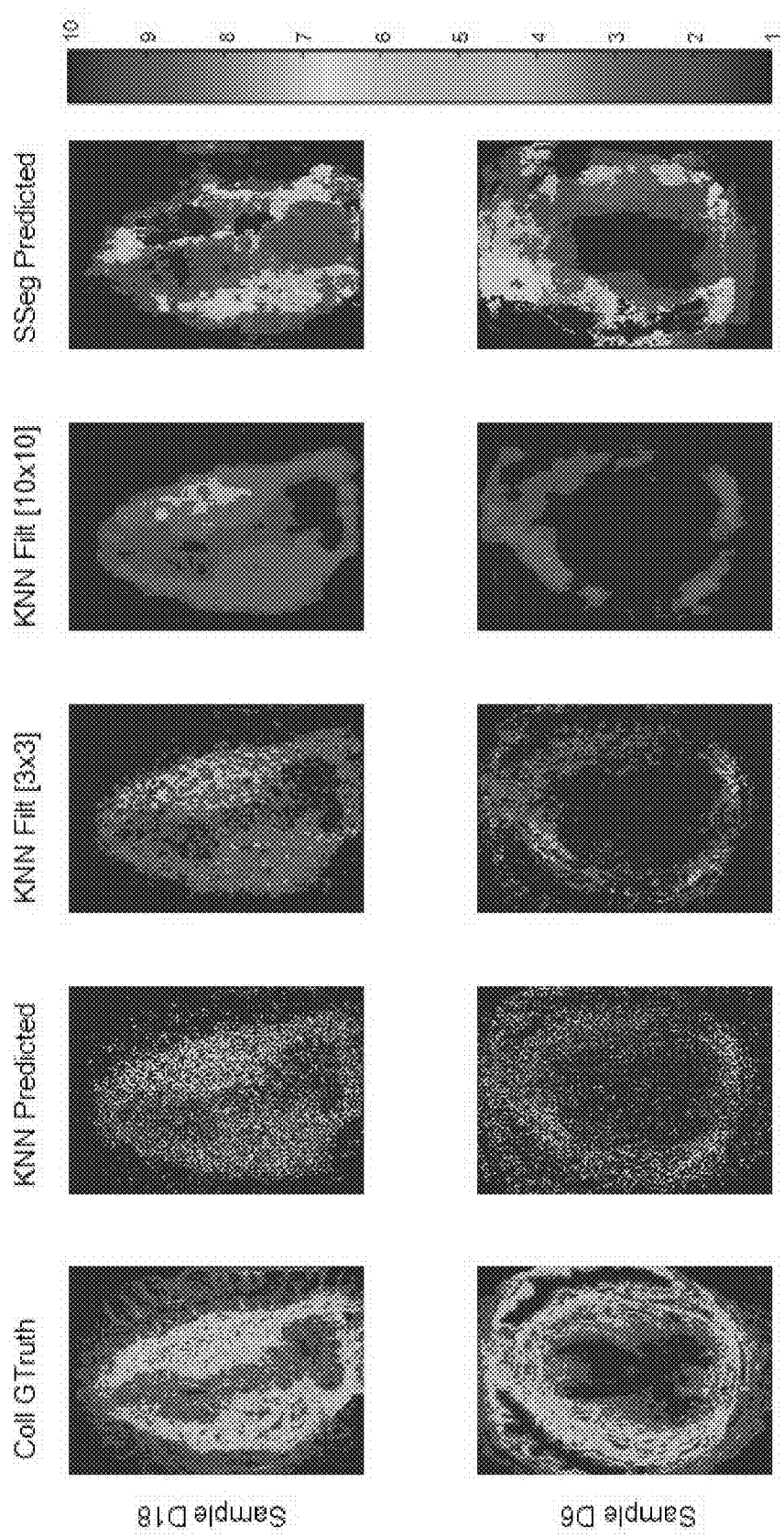
FIG. 8 shows images of collagen classification of samples D18 (first row, labeled "Sample D18") and D6 (second row (labeled "Sample D6"), using a K-NN algorithm and semantic segmentation classification ground truth (first column, labeled "Coll GTruth"), K-NN predicted images (second column, labeled "KNN Predicted"), K-NN predicted images with a median filter [3×3] applied (third column, labeled "KNN Filt [3×3]"), K-NN predicted images with a median filter [10×10] applied (fourth column, labeled "KNN Filt [10×10]"), and semantic segmentation predicted images (fifth column, labeled "SSeg Predicted"). The intensity (reference bar at right side of figure) reflects the density of the respective tissue in the sample.
Figure 9:
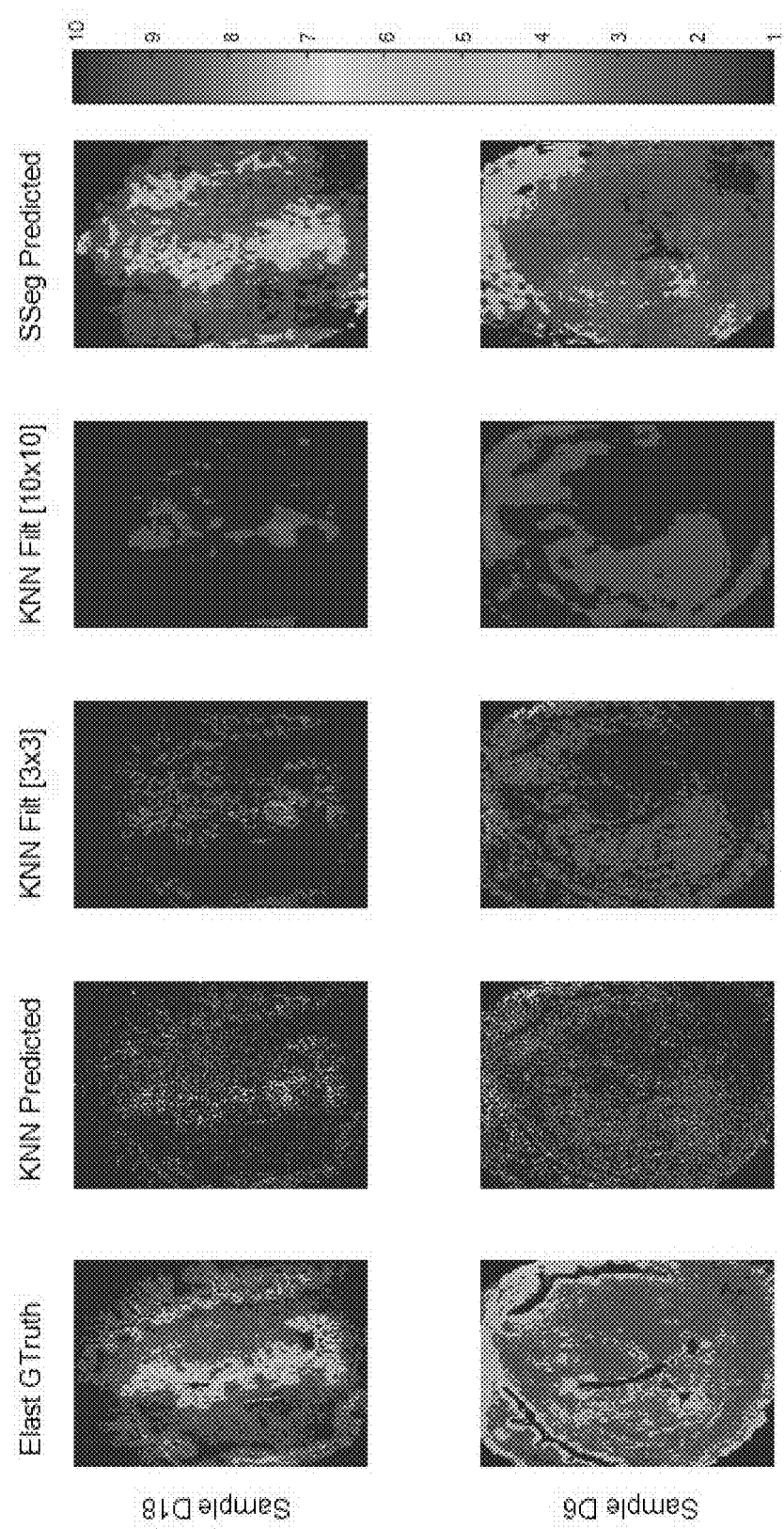
FIG. 9 shows images of elastin classification of samples D18 (first row, labeled "Sample D18") and D6 (second row (labeled "Sample D6"), using a K-NN algorithm and semantic segmentation classification ground truth (first column, labeled "Elast GTruth"), K-NN predicted images (second column, labeled "KNN Predicted"), K-NN predicted images with a median filter [3×3] applied (third column, labeled "KNN Filt [3×3]"), K-NN predicted images with a median filter [10×10] applied (fourth column, labeled "KNN Filt [10×10]"), and semantic segmentation predicted images (fifth column, labeled "SSeg Predicted"). The intensity (reference bar at right side of figure) reflects the density of the respective tissue in the sample.

Visual results are presented in FIGS. 7, 8, and 9 for two samples—"D18" (on day 18 of pregnancy) and "D6" (on day 6 of pregnancy)—for collagen and elastin predictions, and for K-NN and semantic segmentation classifiers. The accuracy table in FIG. 10 presents the average of all the samples on each of the three metrics, for the semantic segmentation and the K-NN classifiers with filters.

Data used for classification included the Muller Matrix component and decompositions described herein, with the data channels of the voxel including diattenuation, depolarization coefficient, linear retardation, differential diattenuation, orientation, differential depolarization, and all Muller Matrix elements except $M_{22}$, $M_{33}$, and $M_{44}$. The four most relevant types of data (linear retardation, $M_{11}$, $M_{34}$, and $M_{43}$) are presented in FIG. 7, along with the SHG and TPEF used as ground truths.

Classification for collagen is shown in FIG. 8, and classification for elastin is shown in FIG. 9. In each figure, the first column presents the original image that was used as a ground truth (SHG for collagen and TPEF for elastin) while the second column presents the K-NN prediction pixel-by-pixel where errors are seen as salt-and-pepper noise. The next two columns show the K-NN prediction with two different applied filters, and the last column presents the semantic segmentation prediction. All images were normalized, and pixels were scaled from 1 to 10, with 1 defined as low density of the tissue and 10 a high density of the tissue.

In general, structures on collagen predictions presented less noise than structures on elastin predictions. The K-NN predictions had significant salt-and-pepper noise that was removed by a mean [3×3] filter. The K-NN prediction with a mean filter of [10×10] provided general areas in which the tissue structures are contained, but lacked resolution.

The table in FIG. 10 summarizes the classification results for independent classification of collagen and elastin. Overall, semantic segmentation gave the best result, notably in SSIM with an accuracy of 93.53% and 91.87% for collagen and elastin, respectively.

Although the small number of samples is a limitation, the three metrics yielded overall good results. Notably, comparing to K-NN the semantic segmentation classifier is more robust and less sensitive to noise.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for visualizing elastin and collagen in tissue, the system comprising:
 a processor; and
 a machine-readable medium in operable communication with the processor and having instructions stored thereon that, when executed by the processor, perform the following steps:
 receiving imaging data of the tissue;
 extracting from the imaging data a ground truth for collagen in the tissue and a ground truth for elastin in the tissue;
 extracting Mueller matrix data from the imaging data to generate a voxel of the imaging data;

utilizing a neural network on the voxel to extract features and generate a feature matrix of the imaging data; and applying at least one classifier to the feature matrix to generate a predicted image to visualize the elastin and the collagen in the tissue.

2. The system according to claim 1, the instructions when executed further performing the following step:

before utilizing the neural network, training the neural network using the ground truth for collagen, the ground truth for elastin, and the voxel.

3. The system according to claim 1, the instructions when executed further performing the following step:

before applying the at least one classifier, training the at least one classifier using the ground truth for collagen and the ground truth for elastin.

4. The system according to claim 1, the instructions when executed further performing the following steps:

transforming the ground truth for collagen and the ground truth for elastin into a ground truth vector;

before utilizing the neural network, training the neural network using the ground truth vector and the voxel; and before applying the at least one classifier, training the at least one classifier using the ground truth vector.

5. The system according to claim 1, the at least one classifier comprising a machine vision classifier.

6. The system according to claim 1, the at least one classifier comprising a K-nearest neighbor classifier and a semantic segmentation neural network.

7. The system according to claim 1, the neural network being a convolutional neural network (CNN).

8. The system according to claim 1, the instructions when executed further performing the following step:

comparing the visualized elastin and collagen in the tissue to the ground truth for collagen and the ground truth for elastin, using at least one of mean square error (MSE), peak signal-to-noise ratio (PSNR), and structural similarity (SSIM).

9. The system according to claim 1, the extracting of the ground truth for collagen and the ground truth for elastin comprising using second harmonic generation (SHG) and two photon excitation fluorescence (TPEF).

10. The system according to claim 9, the SHG being used to extract the ground truth for collagen, and the TPEF being used to extract the ground truth for elastin.

11. The system according to claim 1, the instructions when executed further performing the following step:

before utilizing the neural network and before applying the at least one classifier, removing outliers from the voxel, the ground truth for collagen, and the ground truth for elastin.

12. The system according to claim 1, the instructions when executed further performing the following step:

before utilizing the neural network and before applying the at least one classifier, normalizing the voxel, the ground truth for collagen, and the ground truth for elastin.

13. The system according to claim 1, the voxel comprising data channels, and the data channels of the voxel respectively comprising diattenuation of the Mueller matrix data, depolarization coefficient of the Mueller matrix data, linear retardation of the Mueller matrix data, differential diattenuation of the Mueller matrix data, orientation of the Mueller matrix data, differential depolarization of the Mueller matrix data, and all Muller Matrix elements of the Mueller matrix data except $M_{22}$, $M_{33}$, and $M_{44}$.

14. A method for visualizing elastin and collagen in tissue, the system comprising:

receiving, by a processor, imaging data of the tissue;

extracting, by the processor, from the imaging data a ground truth for collagen in the tissue and a ground truth for elastin in the tissue;

extracting, by the processor, Mueller matrix data from the imaging data to generate a voxel of the imaging data;

utilizing, by the processor, a neural network on the voxel to extract features and generate a feature matrix of the imaging data; and applying, by the processor, at least one classifier to the feature matrix to generate a predicted image to visualize the elastin and the collagen in the tissue.

15. The method according to claim 14, further comprising:

transforming the ground truth for collagen and the ground truth for elastin into a ground truth vector;

before utilizing the neural network, training the neural network using the ground truth vector and the voxel; and before applying the at least one classifier, training the at least one classifier using the ground truth vector.

16. The method according to claim 14, the at least one classifier comprising a K-nearest neighbor classifier and a semantic segmentation neural network, and the neural network being a convolutional neural network (CNN).

17. The method according to claim 14, the extracting of the ground truth for collagen and the ground truth for elastin comprising using second harmonic generation (SHG) and two photon excitation fluorescence (TPEF), the SHG being used to extract the ground truth for collagen, and the TPEF being used to extract the ground truth for elastin.

18. The method according to claim 14, further comprising:

before utilizing the neural network and before applying the at least one classifier, removing outliers from the voxel, the ground truth for collagen, and the ground truth for elastin; and before utilizing the neural network and before applying the at least one classifier but after removing the outliers, normalizing the voxel, the ground truth for collagen, and the ground truth for elastin.

19. The method according to claim 14, the voxel comprising data channels, and the data channels of the voxel respectively comprising diattenuation of the Mueller matrix data, depolarization coefficient of the Mueller matrix data, linear retardation of the Mueller matrix data, differential diattenuation of the Mueller matrix data, orientation of the Mueller matrix data, differential depolarization of the Mueller matrix data, and all Muller Matrix elements of the Mueller matrix data except $M_{22}$, $M_{33}$, and $M_{44}$.

20. A system for visualizing elastin and collagen in tissue, the system comprising:

a processor; and a machine-readable medium in operable communication with the processor and having instructions stored thereon that, when executed by the processor, perform the following steps:

receiving imaging data of the tissue;

extracting from the imaging data a ground truth for collagen in the tissue and a ground truth for elastin in the tissue;

extracting Mueller matrix data from the imaging data to generate a voxel of the imaging data;

removing outliers from the voxel, the ground truth for collagen, and the ground truth for elastin to generate a post-outlier voxel, a post-outlier ground truth for collagen, and a post-outlier ground truth for elastin;

normalizing the post-outlier voxel, the post-outlier ground truth for collagen, and the post-outlier ground truth for elastin to generate a normalized voxel, a normalized ground truth for collagen, and a normalized ground truth for elastin;

transforming the normalized ground truth for collagen and the normalized ground truth for elastin into a ground truth vector;

training a neural network using the ground truth vector and the normalized voxel;

utilizing the neural network on the normalized voxel to extract features and generate a feature matrix of the imaging data;

training at least one classifier using the ground truth vector;

applying the at least one classifier to the feature matrix to generate a predicted image to visualize the elastin and the collagen in the tissue; and comparing the visualized elastin and collagen in the tissue to the normalized ground truth for collagen and the normalized ground truth for elastin, using at least one of mean square error (MSE), peak signal-to-noise ratio (PSNR), and structural similarity (SSIM), the at least one classifier comprising a K-nearest neighbor classifier and a semantic segmentation neural network, the neural network being a convolutional neural network (CNN), the extracting of the ground truth for collagen and the ground truth for elastin comprising using second harmonic generation (SHG) and two photon excitation fluorescence (TPEF), the SHG being used to extract the ground truth for collagen, the TPEF being used to extract the ground truth for elastin, the voxel comprising data channels, the data channels of the voxel respectively comprising diattenuation of the Mueller matrix data, depolarization coefficient of the Mueller matrix data, linear retardation of the Mueller matrix data, differential diattenuation of the Mueller matrix data, orientation of the Mueller matrix data, differential depolarization of the Mueller matrix data, and all Muller Matrix elements of the Mueller matrix data except $M_{22}$, $M_{33}$, and $M_{44}$, and the tissue being cervical tissue.

* * * * *